(12) United States Patent
Sarem et al.

(10) Patent No.: US 6,271,027 B1
(45) Date of Patent: Aug. 7, 2001

(54) CELL AND TISSUE CULTURE DEVICE WITH ENHANCED CULTURE FLUID FLOW

(75) Inventors: Farzin Sarem; Leila-Ouassila Sarem Damerdji, both of Vandoeuvre-les-Nancy (FR)

(73) Assignee: Cell Tissue Progress, Paris (FR)

( * ) Notice: Subject to any disclaimer, the term of this patent is extended or adjusted under 35 U.S.C. 154(b) by 0 days.

(21) Appl. No.: 09/666,592

(22) Filed: Sep. 20, 2000

(30) Foreign Application Priority Data

Jan. 17, 2000 (FR) .................................................. 00 00548

(51) Int. Cl.[7] .................................................... C12N 5/00
(52) U.S. Cl. ......................... 435/325; 435/383; 435/395; 435/286.5; 435/286.6; 435/294.1; 435/305.2
(58) Field of Search ............................. 435/286.5, 286.6, 435/288.5, 294.1, 305.2, 325, 383, 395

(56) References Cited

U.S. PATENT DOCUMENTS 3,860,489 * 1/1975 Cooper, III .

6,042,789 * 3/2000 Antonenko et al. ................... 422/99

FOREIGN PATENT DOCUMENTS

WO 8700548 1/1987 (WO) .
WO 9612789 5/1996 (WO) .

* cited by examiner

Primary Examiner—David A. Redding
(74) Attorney, Agent, or Firm—Young & Thompson

(57) ABSTRACT

A cell and tissue culture device comprises several culture wells (18-i) accommodating cells and tissues to be grown, of first (2) and second (25) tanks, and connecting means (20,23,24) coupled to wells and tanks so as to enable a culture fluid to flow from one tank to another via the wells. Each tank (20,25) accommodates at least a flexible pocket (6,7;27,29), at least one of which is able to receive the culture fluid. The device further comprises at least a controller module (50,150) providing first and/or second sequences of external pressures to be applied, on the pockets of first and second tanks, respectively, and pressurization means (41,46–49) configured for applying to the pockets, pressures defined by said first and second sequences provided by the controller module.

34 Claims, 9 Drawing Sheets

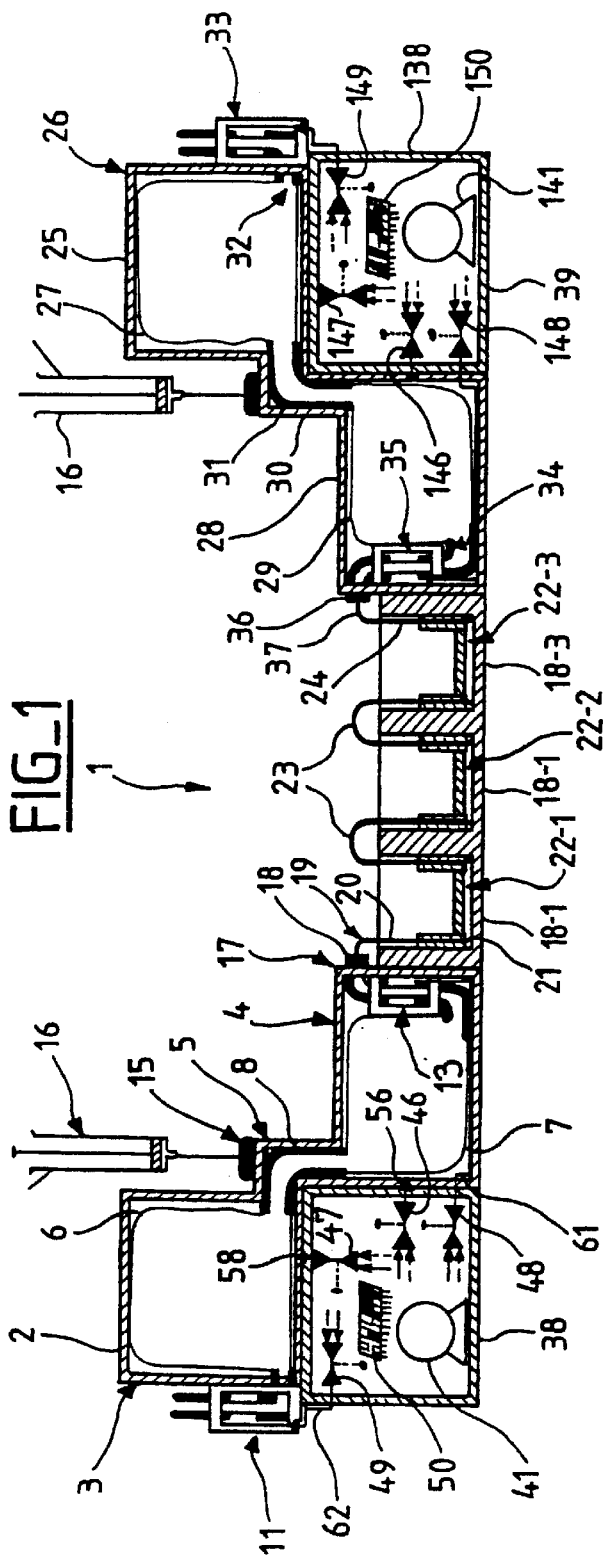
FIG_1
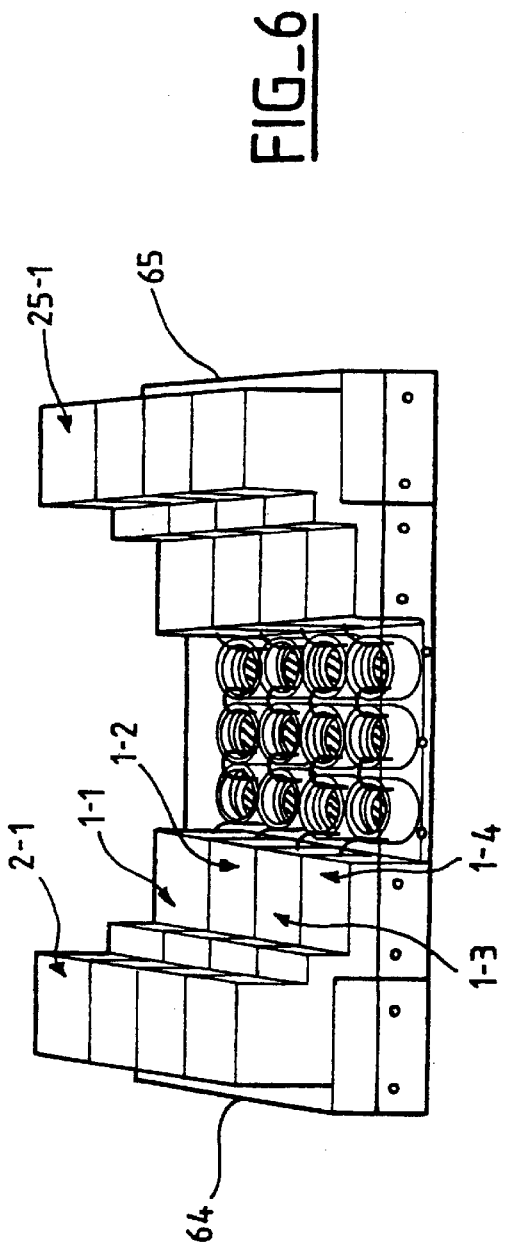
FIG_6

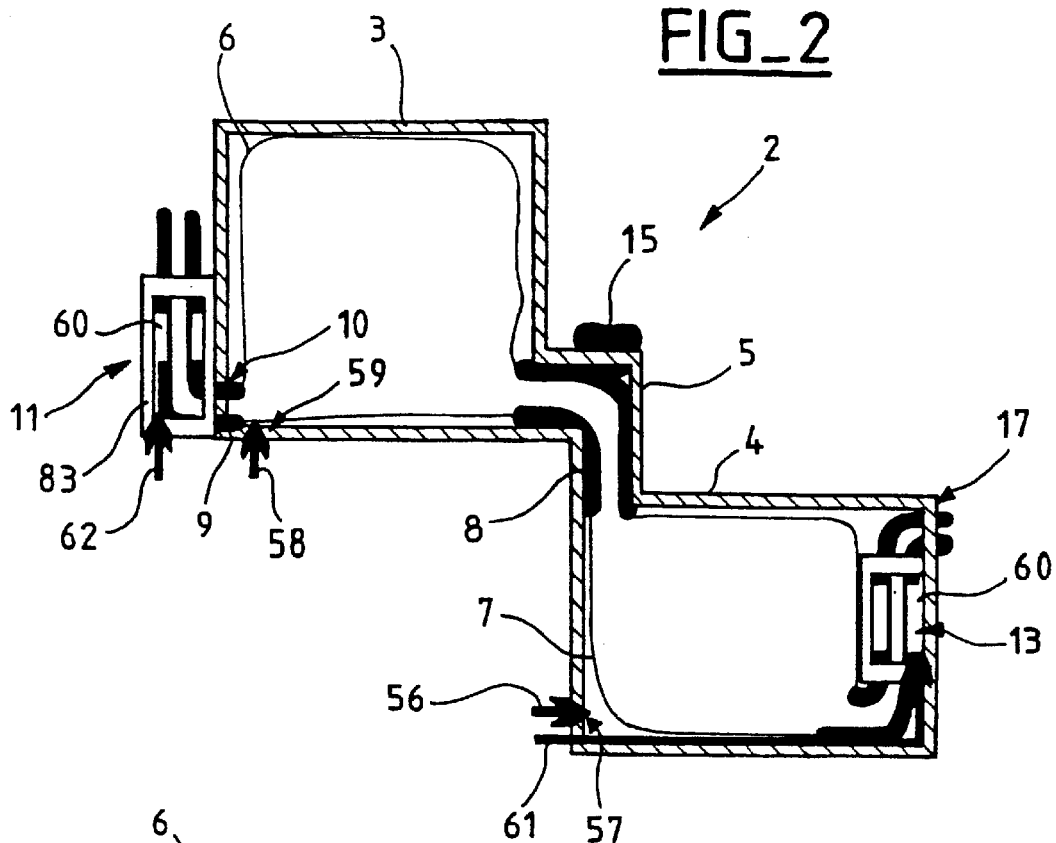
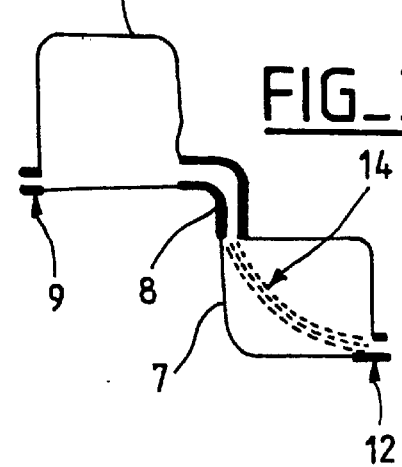
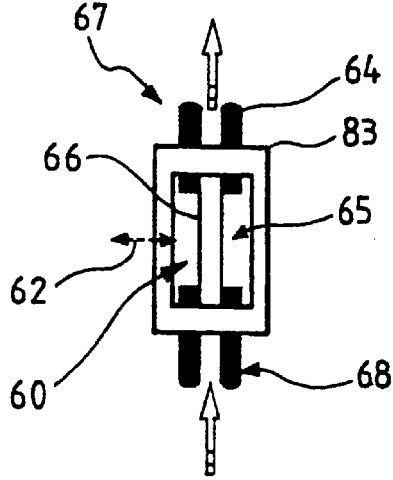
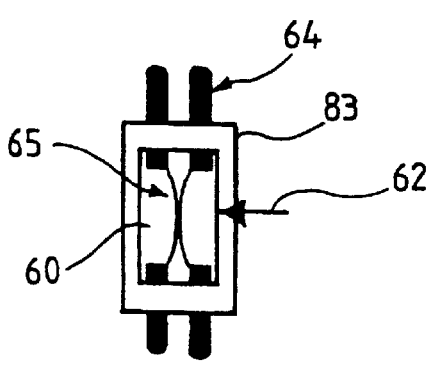

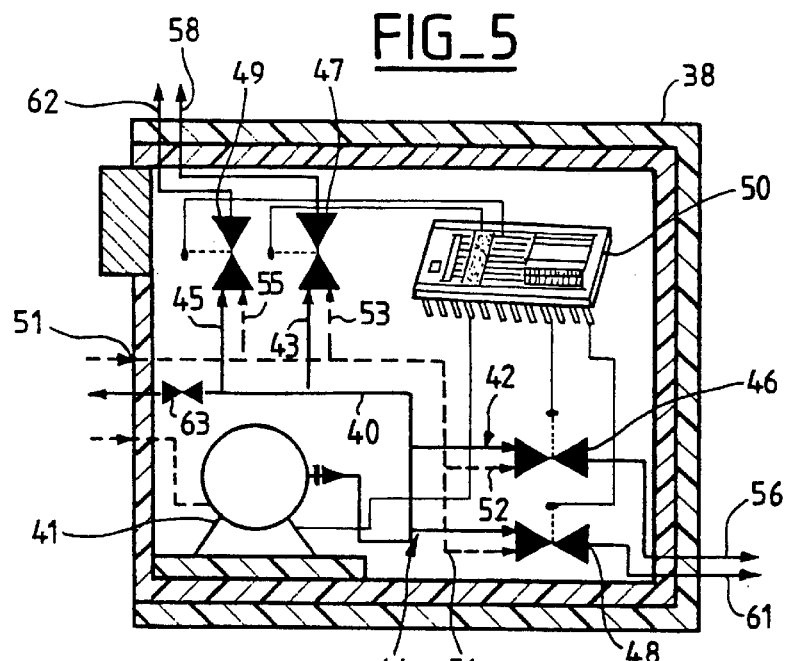
FIG_5
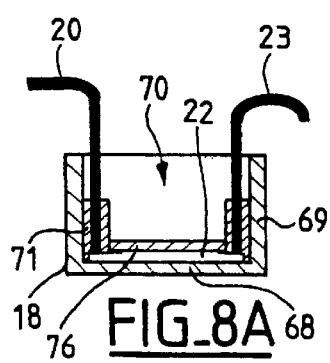
FIG_8A
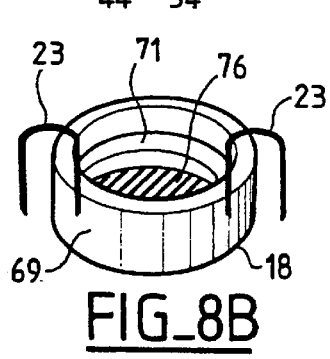
FIG_8B
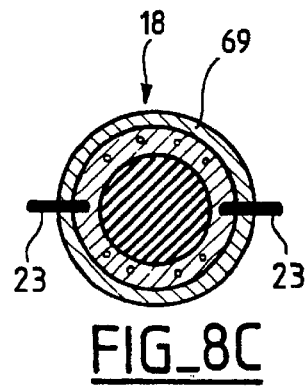
FIG_8C
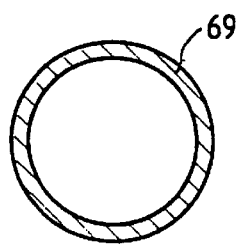
FIG_8D
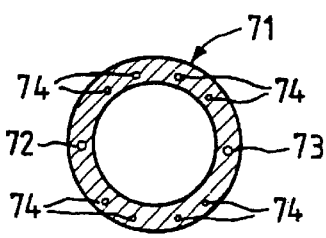
FIG_8E
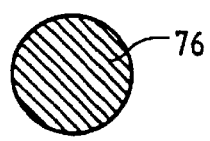
FIG_8F
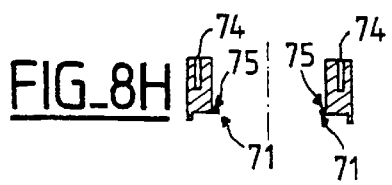
FIG_8H
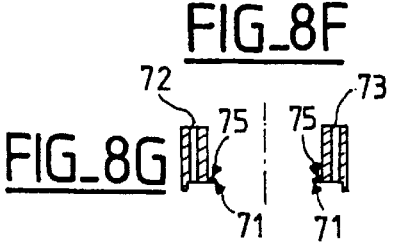
FIG_8G

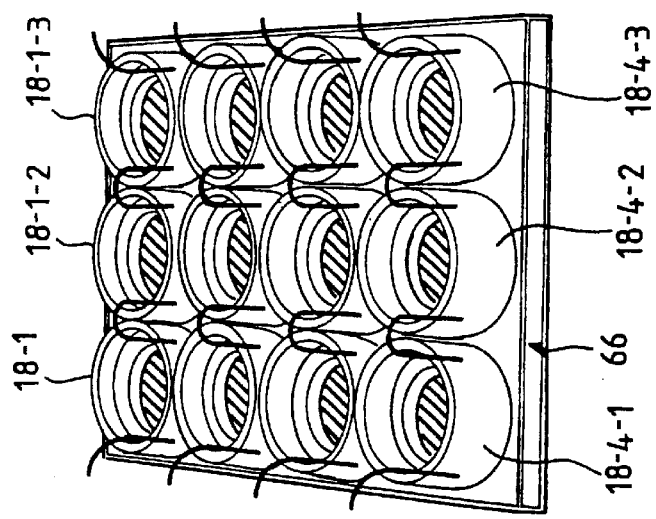
FIG_7B
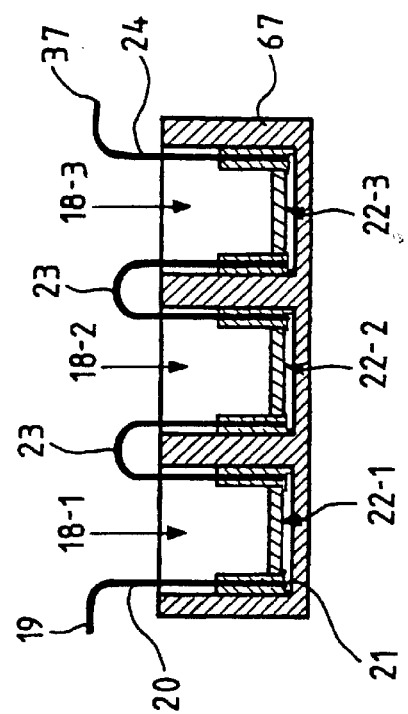
FIG_9
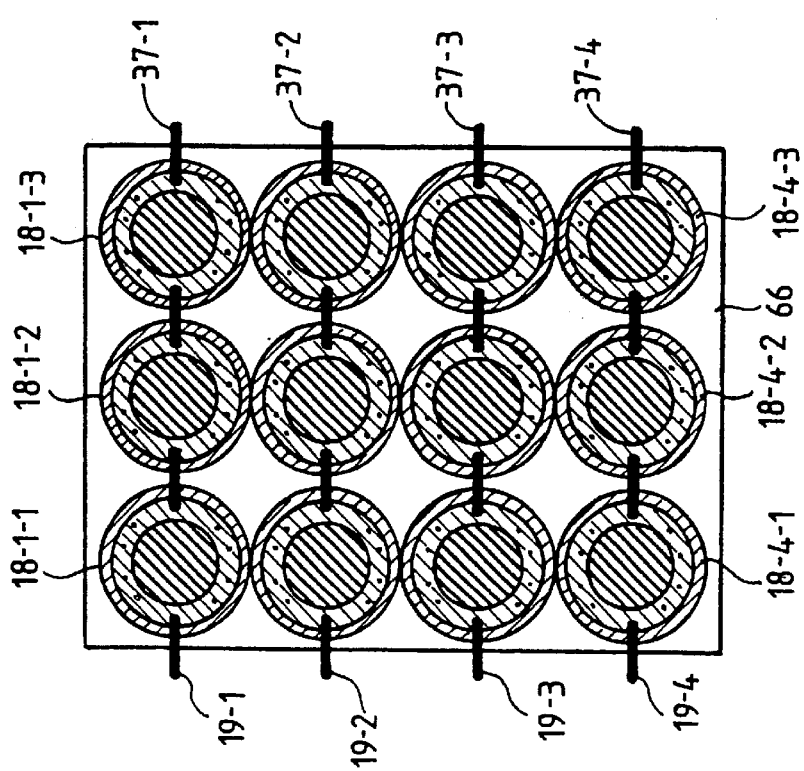
FIG_7A

FIG_10A
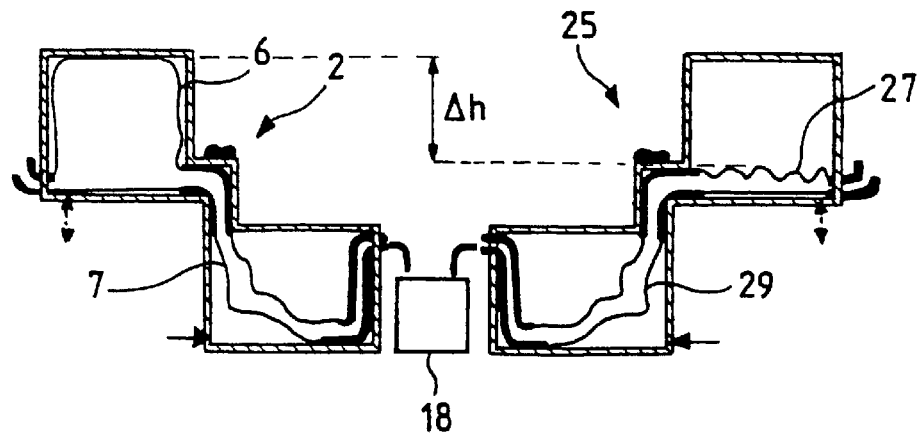
FIG_10B
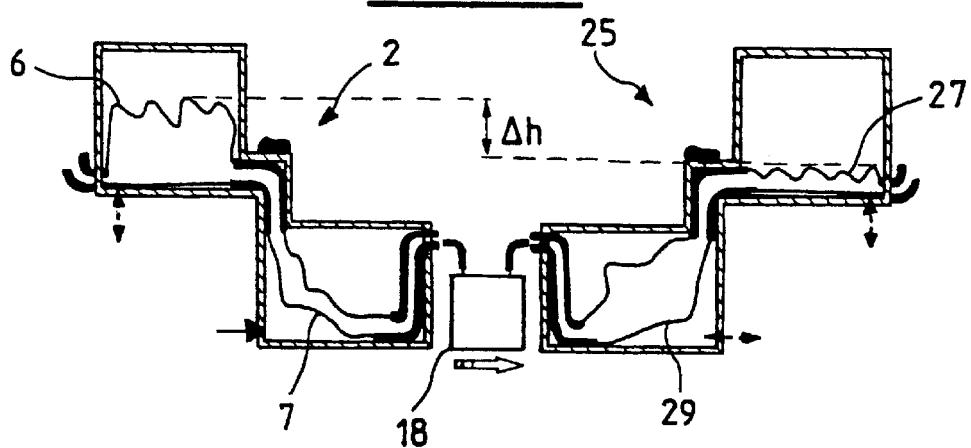
FIG_10C
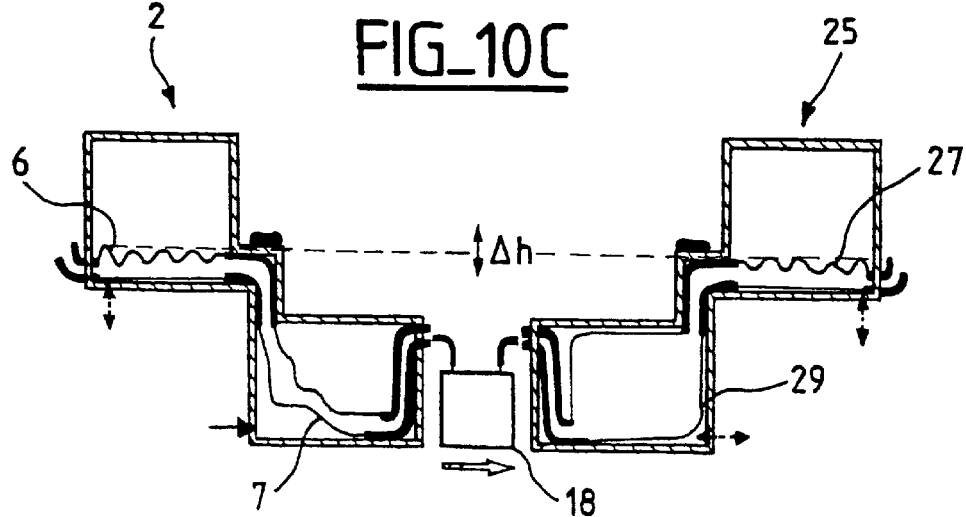

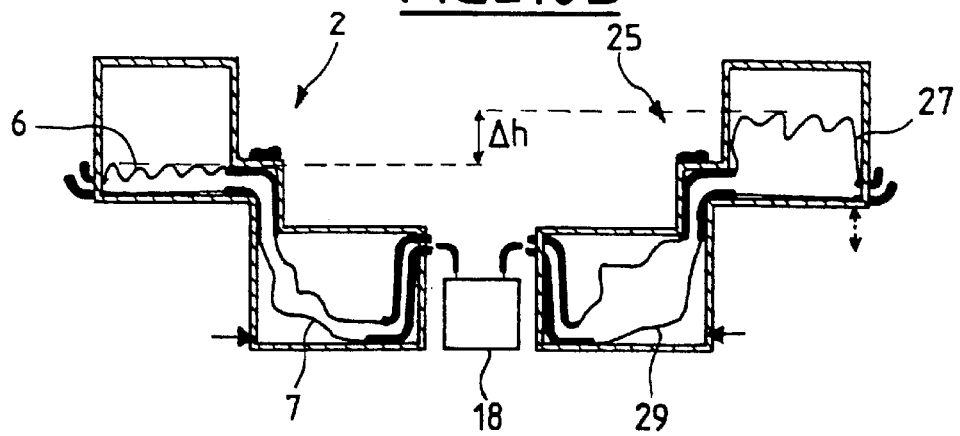
FIG_10D
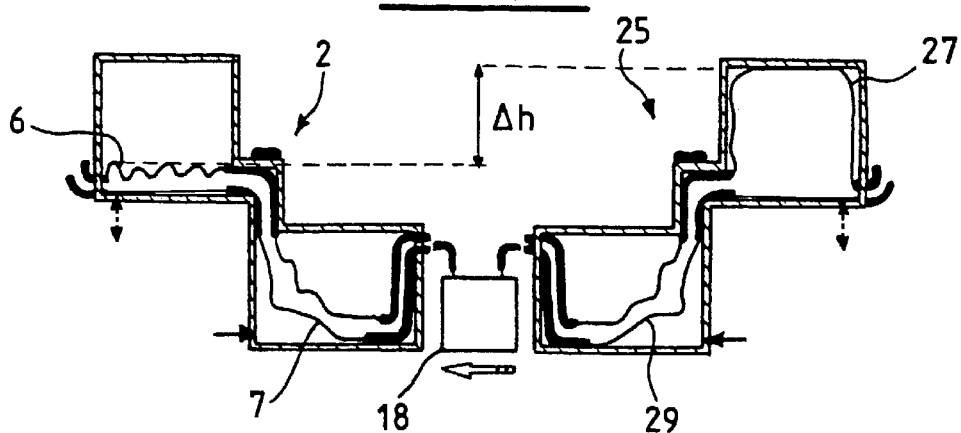
FIG_10E
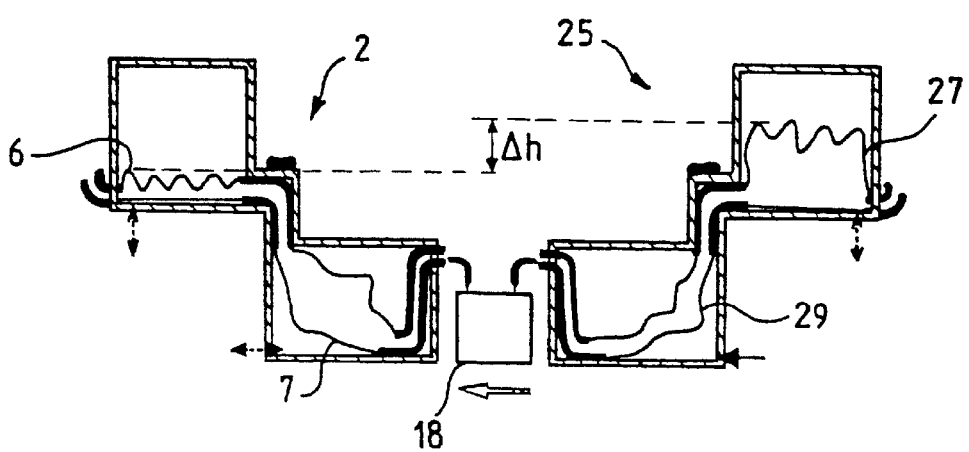
FIG_10F

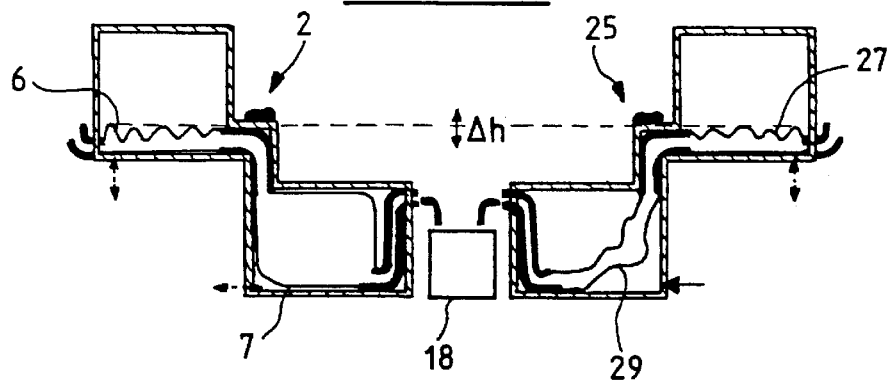
FIG_10G
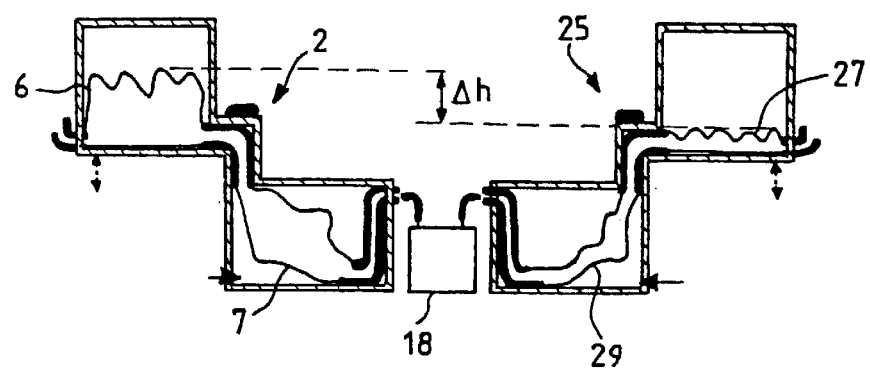
FIG_10H
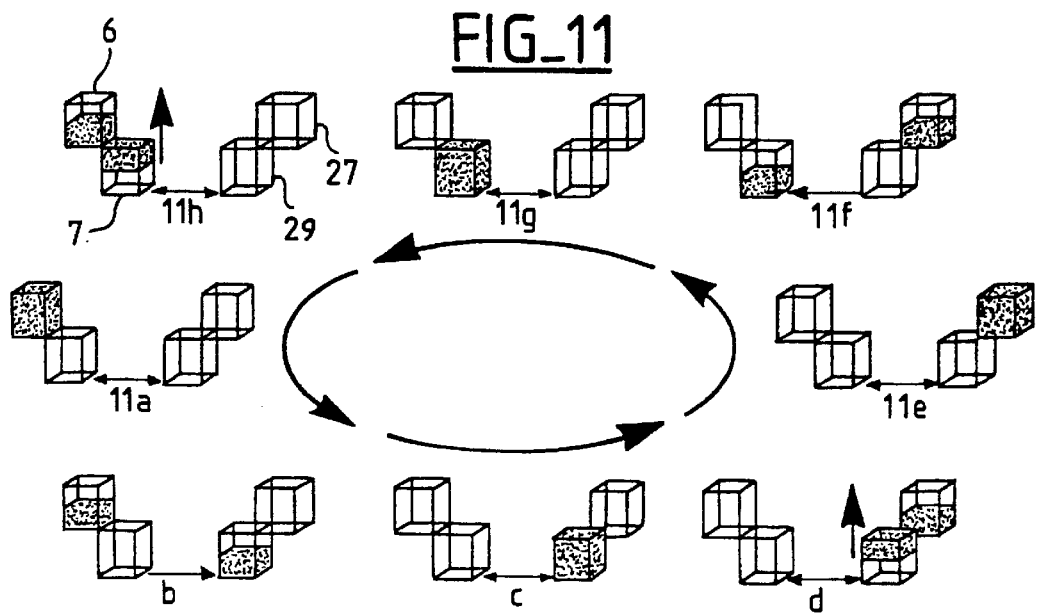
FIG_11

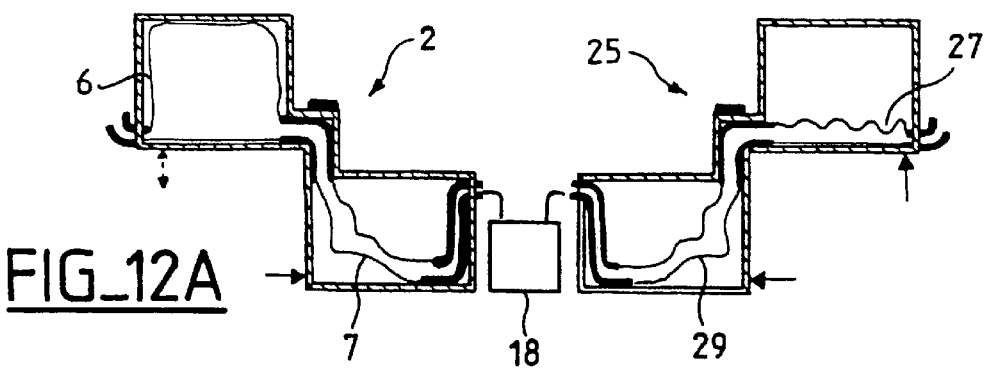
FIG_12A
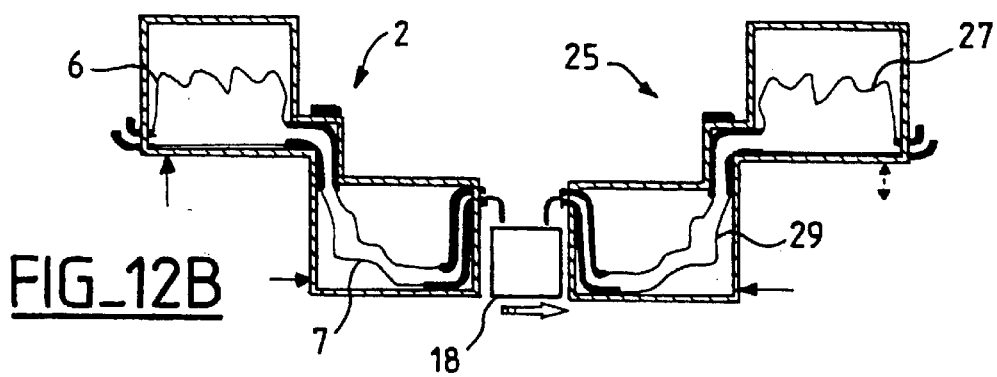
FIG_12B
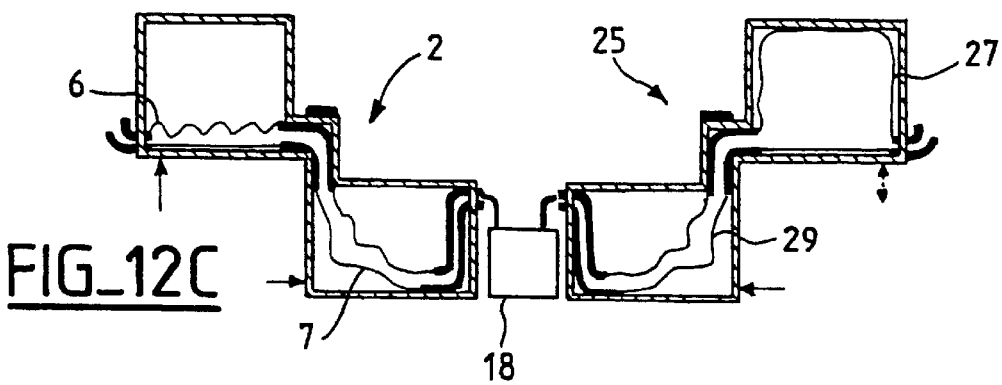
FIG_12C
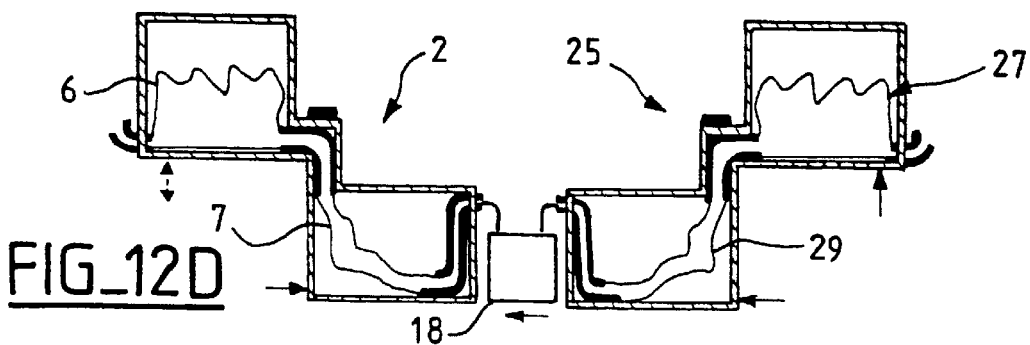
FIG_12D

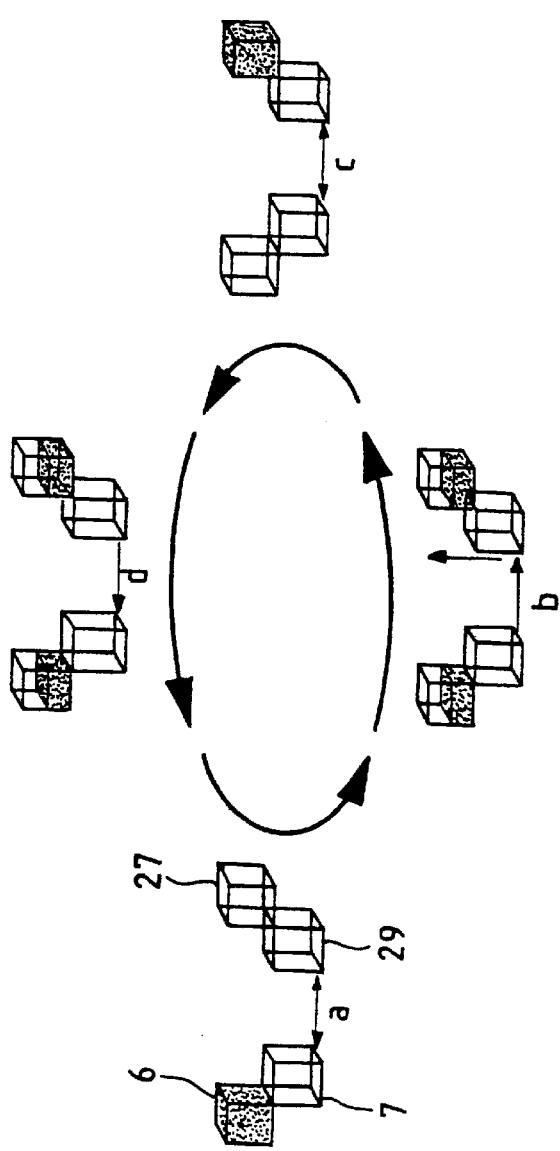
FIG_13
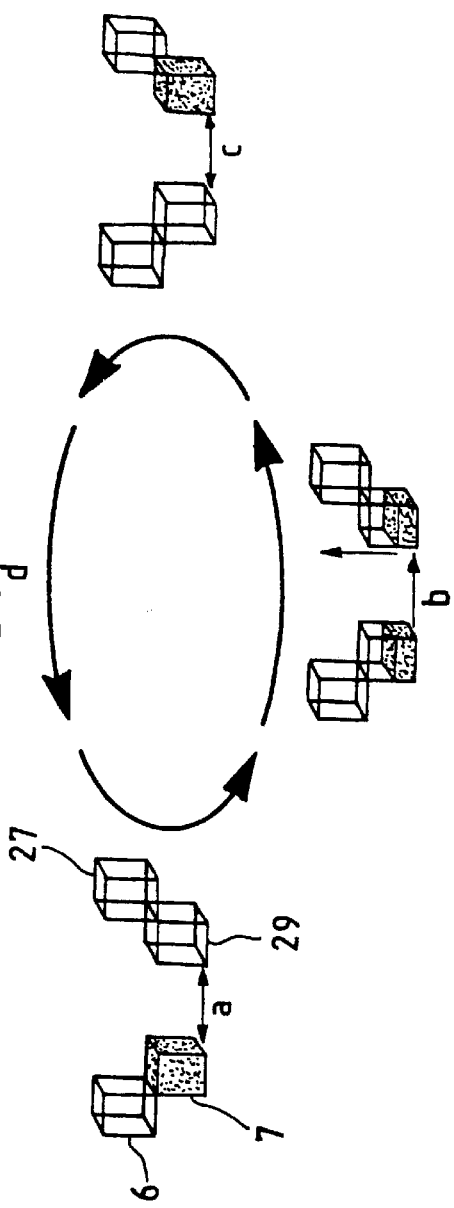
FIG_14

CELL AND TISSUE CULTURE DEVICE WITH ENHANCED CULTURE FLUID FLOW

The invention relates to the field of cell and tissue culture with the help of a culture fluid or nutrient medium.

This invention more particularly relates to devices and methods for cell and tissue culture in which the culture fluid (or nutrient) is set into motion so as to achieve a dynamic culture. Such devices usually apply either a technique for directly stirring the culture fluid in the culture volume or a technique providing permanent flow of the fluid through a specific circuit.

The present invention is more specifically directed to fluid flow devices which comprise at least a culture well defining a chamber in which cells or tissues to be grown are accommodated, first and second tanks, at least one of which is configured so as to receive a culture fluid, as well as connecting means coupling the well to the first and second tanks. The culture fluid flows from one tank to the other via the well.

This technique for fluid flow is difficult to control because culture conditions change over time. Actually, the low cell concentration which exists at the beginning of the culture process, requires a quasi-static environment, and therefore a very low culture fluid flow rate. Then the flow rate rapidly increases because of cell multiplication or tissue growth.

Maintaining adequate conditions during the whole culture process requires either the use of several suitable devices, at different stages of the culture's growth, respectively, and this involves many handling operations, or complex and often cumbersome means, which limit, even preclude observation of the culture's development with a microscope. These handling operations and means are all the more complex as the culture process should be carried out in a sterile environment which requires highly qualified personnel, and this therefore increases the cost for each culture. Furthermore, because of their price, these devices should be reusable, which imposes complete sterilization before each new culture, and maintenance operations.

The object of the invention is therefore to overcome all or part of the aforementioned drawbacks.

For this purpose, it provides a device of the type described in the introduction wherein each of the first and second tanks accommodates at least a flexible pocket, wherein at least one of the pockets of these tanks is adapted for receiving the culture fluid, and which comprises at least a control means able to provide first and/or second sequences of external pressures to be applied, on the pockets of the first and second tanks, respectively, and pressurization means configured for applying to the pockets, whereby the pressures are defined by the first and second sequences provided by the controller module.

So, defining for each type of culture, pressure sequences to be applied on the different pockets, then transferring these sequences to the controller module is sufficient for carrying out the culture process throughout its duration in adequate conditions. This transfer may indirectly be made through an entry interface, or else directly through a memory in which a multiplicity of sequences matching different samples, is stored beforehand (this memory may possibly be rewritable through the aforementioned interface).

In a preferred embodiment of the device according to the invention, the first and second tanks each comprise an upper portion and a lower portion which are connected to each other through an intermediate narrow portion and each accommodate a flexible pocket, wherein the upper and lower flexible pockets communicate with each other via the intermediate portion, and connecting means communicating with the lower pockets.

In this embodiment, it is particularly advantageous that the controller module be able to provide pressure sequences suitable for each pocket, so that the pressurization means apply on each of these pockets the pressures from the sequences that match them.

The device according to the invention may include additional characteristics considered separately or combined and notably:

At least one of the first and second tanks may include an opening adapted for introducing culture fluid into the communication duct between pockets;

at least one of the upper portions of the tanks may include an upper opening for connecting the upper pocket, which it accommodates, to a culture fluid feeding and extraction device;

first access control means, driven by the controller module may control access to the upper pocket via the upper port;

each lower tank portion may include a lower port for connection of connecting means to the lower pocket which it accommodates, and second access control means, driven by the controller module, may control access to the lower pockets via the lower ports;

the upper and lower portions of the first and second tanks may each include a leak-proof inlet, and the pressurization means may comprise a first pressurization circuit supplying with high pressure fluid, under control of lower and upper valves driven by the controller module, each upper and lower portion of the first and second tanks, via the leak-proof inlets;

the upper and lower portions of the first and second tanks may each include a leak-proof inlet, and the pressurization means may comprise, on the one hand, a first pressurization circuit including a fluid pump (or compressor) and supplying with high pressure fluid, under the control of upper and lower valves driven by the controller module, each upper and lower portion of the first tank via the leak-proof inlets, and on the other hand, a second pressurization circuit including a fluid pump and supplying with high pressure fluid, under the control of upper and lower valves driven by the controller module, each upper and lower portion of the second tank, via the leak-proof inlets;

each pressurization circuit may also comprise two other valves respectively cooperating with the first and second access control means, which are then advantageously provided with a duct including a flexible thinned area on which the high pressure fluid may act the pressurization means may also include a third pressurization circuit supplying with low pressure fluid, under the control of upper and lower valves, each upper and lower portion of the first and second tanks, via leak-proof inlets. Alternatively the pressurization means may include a third pressurization circuit supplying with low pressure fluid, under the control of said upper and lower valves, each upper and lower portion of the first tank, via the leak-proof inlets, as well as a fourth pressurization circuit supplying with low pressure fluid, under the control of upper and lower valves, each upper and lower portion of the second tank, via the leak-proof inlets. In each case, each third and fourth pressurization circuit is advantageously connected to the other valves so as to cooperate with the first and second access control means;

at least two wells may be placed in series by having them communicate through connecting means, wherein each of these wells is connected to the first tank and the other well is connected to the second tank. A third or even a fourth or fifth well may be placed in series between the two other wells;

the wells may be provided as independent units assembled together, or they may be configured on a culture plate;

each culture chamber may include at least a transparent wall for observation of cells and tissues during the culture process, for example under a microscope;

each well may be configured so as to define two superimposed culture chambers separated by a filter.

In addition, the invention relates to a cell and tissue culture facility comprising at least two devices of the type described above, placed in parallel, and including a single control unit driving together the control units of these devices.

The invention also relates to a cell and tissue culture method. This method starts with a known first step wherein a culture device is provided including at least a culture well for receiving the cells or tissues to be grown, with first and second tanks coupled to the well, at least one of which is configured for receiving culture fluid. Said method is characterized by the fact that in the first step, at least a flexible pocket of which at least one may receive the culture fluid, is accommodated in each tank, and by the fact that it consists of a second step in which pressures defined in the first and second sequences of selected pressures are applied to the pockets, in order to control culture fluid flow in the well(s).

Preferably, in the first step, an upper portion and a lower portion connected with each other through an intermediate narrow portion and each accommodating a flexible pocket, are provided in each tank. The upper and lower pockets of each tank communicate with each other via the intermediate portion and the lower pockets are coupled to the well. Furthermore, in the second step, pressures defined by first sequences of selected upper and lower pressures are applied on the upper and lower pockets of the first tank, respectively, and pressures defined by second sequences of selected lower and upper pressures are applied on the lower and upper pockets of the second tank, respectively.

Two main application modes for the second step may be considered according to the required culture fluid flow rate. In a first mode, a so-called "laminar" mode, most particularly adapted to low flow rates, the culture fluid is forced to rise in the upper pocket of one of the tanks, so that it is placed at a higher level than that of the lower pocket of the other tank, then it is left to reach this lower pocket of the other tank, by forcing it to cross the well(s) consequently. The fluid is then forced to rise in the upper pocket, then transfer towards the other upper pocket is performed in the reverse direction. This reciprocating motion is repeated a selected number of times. This mode is most particularly suited to non-adhering cells insofar that, the culture fluid flux being very low and the cells, despite all of this, having a non-zero adhesion coefficient to the culture chamber's walls, these cells are not carried away by the fluid flux from one culture chamber to the other.

In a second mode, so-called "turbulent" mode most particularly suitable for high flow rates, high pressure is permanently applied on both upper or lower pockets and pressure sequences with "opposite phase", formed from alternating periods of high and low pressures, are applied on the lower or upper pockets. In an alternative embodiment, applying a same first sequence of pressures on both upper and lower pockets of a tank simultaneously and a same second sequence of pressures on both upper and lower pockets of the other tank simultaneously, may also be considered, whereby the first and second sequences have opposite phase.

Of course, combination of these different modes with each other may be considered.

Other features and advantages of the invention will become apparent on examining the detailed specification hereafter and the appended drawings, wherein:

FIG. 1 schematically illustrates in a transverse sectional view, a culture device according to the invention, with several chambers, FIG. 2 illustrates in detail, in a transverse sectional view, one of the tanks of FIG. 1, FIG. 3 illustrates in detail in a transverse sectional view, the assembling of both flexible pockets of the tank in FIG. 2, FIGS. 4A and 4B schematically illustrate, in a transverse sectional view, two states of the access control means to the flexible pocket, in a preferred embodiment, FIG. 5 schematically illustrates a block for controlling the pressurization of a tank, FIG. 6 is a schematic perspective view of a culture facility made up from four culture devices placed in parallel, FIGS. 7A and 7B are perspective and top schematic views, respectively of a plate with wells for a facility of the type illustrated in FIG. 6, FIGS. 8A to 8H are schematic views of the main constituents of a well, before and after assembly, FIG. 9 schematically illustrates, in a transverse sectional view, an alternative embodiment for a multi-welled structure, FIGS. 10A to 10H are schematic views illustrating the eight successive phases of a culture fluid reciprocation in a flow mode of the laminar type, FIG. 11 illustrates the sequence of the eight phases of FIGS. 11, FIGS. 12A to 12D are schematic views illustrating the four successive phases of culture fluid reciprocation in a flow mode of the turbulent type, FIG. 13 illustrates the sequence of the four phases of FIG. 12, FIG. 14 is an alternative turbulent mode illustrated in FIGS. 12 and 13.

The appended drawings have essentially a definite character. Accordingly, they may not only serve to complete the invention, but also to contribute to its definition, if need be.

Reference is initially made to FIG. 1 in order to describe a cell and tissue culture device in a non-limiting embodiment.

Device 1 illustrated in FIG. 1 initially comprises a first tank 2 including an upper portion 3 coupled to a lower portion 4 through an intermediate portion 5. Preferably, this tank is delimited by stiff walls which give it a constant volume.

In the illustrated example, the upper portion 3 of the tank accommodates an upper flexible pocket 6. Also, the lower portion 4 accommodates a lower flexible pocket 7 which is connected to the upper pocket 6 through a duct 8 closely accommodated in the intermediate portion 5, so that the upper 3 and lower 4 portions of the first tank 2 are isolated from one another.

As better illustrated in FIGS. 2 and 3, upper pocket 6 includes an inlet/outlet 9 adapted so as to be able to sealably cooperate with an upper port 10 formed in one of the partitions of the upper portion 3 of the first tank 2. The upper pocket 6 may thereby be connected to upper access control means 11, themselves connected to a gas or culture fluid feeding module (not shown).

Also, the lower pocket 7 includes an inlet/outlet 12 adapted for cooperating with a port formed in the wall of the lower portion 4 of the first tank 2, or, as illustrated in FIG. 2, for cooperating with access control means 13 accommodated within the lower portion 4 of tank 2.

Preferably, as illustrated in FIG. 3, the lower pocket 7 may include two substantially stiff membranes 14 which prevents its complete squeezing when it is submitted to very high pressures, which would impair proper flow of the culture fluid.

Also the first tank 2 preferably includes, in the intermediate portion 5, another port 15 for injecting or extracting, manually or automatically, a liquid or a gas within duct 8. Preferably, this is a port 15 equipped with a septum, particularly suitable when the injection or extraction device is a syringe 16 provided with a needle.

Also, upper 6 and lower 7 pockets are preferably made of a porous material, at least in the direction pointing from the outside to the inside. This may be silicone or polydimethylsiloxane (PDSM) or even polytetra-fluorethylene (PTFE), or even dimethyl- and methylvinyl-siloxane polymer pockets. Actually this provides gas exchanges between the culture fluid which is accommodated within the flexible pockets and the gas which is trapped within the upper 3 and lower 4 portions of the first tank 2.

In the example illustrated in FIG. 1, the lower pocket 7 communicates with culture wells 18-1 to 18-3, via access control means 13 and the lower port 17 formed in the wall of the tank.

More precisely, the access control means 13 include a hollow end 18 in which an end 19 of a connecting means 20 is inserted, provided as a duct (or tube), and the opposite end of which 21 opens into the culture chamber 22-1 of the first well 18-1. This first culture chamber 22-1 communicates with the second culture chamber 22-2 accommodated in the second well 18-2 through another connecting means 23, also provided as a duct (or tube). Similarly, the second culture chamber 22-2 communicates with the third culture chamber 22-3 accommodated in the third well 18-3, through another connecting means 23 provided as a duct (or tube). Finally, in this example, a last connecting means 24 provides communication between the third culture chamber 22-3 and a second tank 25, which will now be described.

Preferably, this second tank 25 is substantially identical to the first tank 2 which was described earlier with reference to FIGS. 1 to 4. It therefore includes, in this example, an upper portion 26 in which an upper flexible pocket 27 is accommodated, a lower portion 28 in which a lower flexible pocket 29 is accommodated and an intermediate narrow portion 30 which accommodates a duct 31 coupling the upper pocket 27 with the lower pocket 29. This duct 31 is also closely accommodated in the intermediate portion 30, so that the upper portion 26 is isolated, imperviously to gas, from the lower portion 28.

Upper pocket 27 includes an adapted inlet/outlet 32, connected to access control means 33, which like access control means 11, may be connected to a fluid or gas feeding device, or to an extractor (not shown). Similarly, lower pocket 29 includes an inlet/outlet 34 which, in the illustrated example, is connected to access control means 35, accommodated within the lower portion 28 of the second tank 25.

Preferably, the second tank 25 also includes, in its intermediate portion 30, another port for injecting or extracting, manually or automatically, a liquid or a gas within duct 31. Preferably, this is a port equipped with a septum. In this example, access control means 35 include a hollow end 36 to which the end 37 of duct 24 is connected.

A circuit is thus created between the upper portion 6 of the first tank and the upper pocket 27 of the second tank 25, via culture chambers 22-i (i=1 to 3, in this example) and via connecting means 20,23 and 24.

For controlling the internal volumes of upper pockets 6 and 27 and of lower pockets 7 and 29, the device according to the invention includes pressurization means which will now be described, with reference to FIGS. 1 and 5.

In the preferred illustrated embodiment, each tank includes its own pressurization means accommodated in a case 38 or 39. These cases are substantially identical, only the one which is coupled to the first tank 2 will be described hereafter.

Case 38 includes a first high pressure pressurization circuit 40, including a pump 41, preferably with a variable flow rate.

This first high pressure circuit 40 includes a first route 42 for supplying with pressurized air, the inside of lower portion 4 of the first tank 2, so as to control the volume of the lower pocket 7.

The first high pressure circuit includes a second route 43 for feeding the inside of the upper portion 3, so as to control the volume of the upper pocket 6.

In the illustrated embodiment, the first high pressure circuit 40 also includes third 44 and fourth 45 routes for controlling the state of access control means 11 and 13, respectively, which will be discussed later on.

Each of these first 42, second 43, third 44 and fourth 45 routes includes a solenoid valve, referenced from 46 to 49 respectively.

All these solenoid valves 46–49 and the pressurization fluid 41 are controlled by a control unit 50, provided as a microprocessor (or micro-controller). The pressurization block 38 also includes a second pressurization circuit 51 (materialized by dotted lines) which opens to the outside world, so as to provide low pressure, equivalent to atmospheric pressure. This second pressuri-zation circuit 51 includes four routes 52 to 55 connected to solenoid valves 46 to 49, respectively, which are therefore of the three route type (two inlets and one outlet).

In this way, the micro-controller 50 is capable of applying low pressures or high pressures according to needs, in the upper 3 and lower 4 portions of the first tank 2.

The outlet of the solenoid valve 48 of the first route 44 feeds, via a duct 56, a port 57 formed in the wall of the lower portion 4 of the first tank 2. Similarly, the outlet of solenoid valve 47 feeds, via a duct 58, a port 59 formed in the wall of the upper portion 3 of said first tank 2. Finally, outlets of solenoid valves 48 and 49 feed housings 60, respectively, which access control means 11 and 13, via ducts 61 and 62, comprise respectively.

These housings are detailed in FIGS. 4A and 4B. In fact, in the illustrated embodiment, the access control means 11,13,33 and 35 comprise a closed and recessed case 63, so as to delimit the internal housing 60 and to receive a tube 64 including, in a central portion 65, accommodated within housing 60, a thinned portion 66, of great flexibility. Both ends 67 and 68 of this tube 64 open outside the housing 60 through ports formed in the case 83, so that they may be connected either to an inlet/outlet 9 or 12 of a flexible pocket 6 or 7, or to the end 19 or 37 of a connecting means 20 or 24, or even to a gas or liquid feeding or extraction device (not shown). However, this is only an exemplary embodiment among others, such as switches or valves.

By applying high pressure on the thinned portion 66 of the tube 64 as illustrated in FIG. 4B, the thinned walls are squeezed preventing any fluid from passing through. In other words, according to whether the pressure applied in housing 60 on the thinned area 66 of tube 64 is high or low, the access control means 11 or 13 is either in a flow on or flow off state (i.e. closed or open), so that it acts as a switch. This switching is not neces-sarily of the on/off control type, although this is preferable. Actually, partial or total squeezing may be achieved according to the pressure intensity applied on the thinned area 66,.

Preferably, the first circuit 40 also includes an additional solenoid valve 63 for regulating the pressurization fluid flow rate. This solenoid valve is also driven by the microcontroller 50.

On the other hand, the pressurization block preferably includes a communication interface, for is example of the RS232 type, enabling said case to be connected to a microcomputer for programming the micro-controller 50.

As indicated earlier, in the illustrated embodiment in FIG. 1, the device according to the invention includes another pressurization block 138 substantially identical with block 38 which has just been described with reference to FIG. 5. The reference numbers for components of this block 13 have the same numbers as those of components of block 38, increased by 100. The pressurization fluid pump thereby has reference 141, the other solenoid valves of the pressurization circuit have numbers 146–149 and the micro-controller has number 150.

Preferably, the two pressurization blocs are independent of one another.

This embodiment is presently preferred, insofar that each pressurization block 38, 138 may be integrated under the upper portion 3, 26 of a first 2 or second tank 25, providing a compact modular assembly. Further, this notably simplifies the pressurization circuits, notably by preventing connection problems.

Of course, in an alternative embodiment, the device according to the invention may only comprise a single pressurization block controlling the applied pressure on each of the flexible pockets of the tanks. In such an alternative, only one single micro-controller may be used for controlling the whole set of solenoid valves of the pressurization circuit. In an another alternative embodiment, a pressurization block may be retained for each tank, but only a single fluid pump and/or a single micro-controller would be used.

As schematically illustrated in FIG. 6, it is possible to position a multiplicity of devices 1 in parallel, so as to form a cell and tissue culture facility with a high yield. In this example, the facility includes four parallel devices 1-1 to 1-4, each device 1-i (i=1 to 4 here) including three culture wells 18-j (j=1 to 3 here) in series. These devices are independent here, but they may cooperate together, for example because of connecting means which couple certain of their wells.

Preferably, in this type of facility, the pressurization means of each device 1-i are accommodated in two cases 64 and 65 for the first tank 2-i and 25-i, respectively, preferably, each case 64, 65 accommodates as many pressurization blocks 38, 138 as there are devices, whereby each block is advantageously independent of the block controlling the tank of the neighboring device. However, in an alternative embodiment, having the case 64 include a single microcontroller for driving the whole set of solenoid valves controlling the different accesses to upper and lower portions of each tank may be considered. There may also be only a single pump.

In such a facility, the number of assembled devices in parallel may vary according to requirements.

In a facility according to the invention, like in a device according to the invention, the culture wells 18-j may be mounted in series on a support plate, as illustrated in FIGS. 7A and 7B, or directly formed by recessing a thick massive block 67 (as illustrated in FIGS. 1 and 9).

In the first example (FIG. 7), the plate may include housings for receiving each well 18-i-j (i=1 to 4, and j=1 to 3 here).

In the second exemplary embodiment, the culture wells of the devices may be provided in independent massive blocks, or in a single block.

Now reference is made to FIGS. 8A to 8H in order to describe a preferred embodiment for the culture wells.

As illustrated in FIG. 8A, a well of the independent type, is delimited by walls, including a bottom preferably planar wall 68, and a preferably cylindrical side-wall 69, although any other type of shape may be considered, according to requirements. These walls 68 and 69 delimit a recess 70 at the bottom of which is placed a flexible ring 71 (see FIGS. 8E and 8G) in which are formed two through openings 72 and 73 providing a passage for collecting means 20, 23 or 24. These connecting means are preferably stiff and they have an external diameter slightly greater than the internal diameter of the openings, so as to provide a quality seal.

Preferably, this flexible ring 71 has the properties of a septum, for multiple injections with needles, inside the culture chamber 22, and without impairing the seal. For example it might be a silicone ring including pre-formed openings 64 delimiting injection points (see FIG. 8H).

The flexible ring 71 includes in its lower portion, on the inside, a substantially circular rim 75, for supporting a preferably transparent lid 76 (see FIG. 8F).

This lid 76 is intended to be secured in recess 70, at a selected distance from the bottom of the well, delimited by wall 68, so as to sealably form a culture chamber 22 wherein the cell or tissue culture will be grown.

The bottom of the well, delimited by the upper side of wall 68, may be treated beforehand according to the specific needs for a cell strain. Such a treatment may be chemical or physical. For example, furthermore, a slide, with or without specific treatment, may be deposited on this wall 68, so as to fix the cells.

Other components whether bio-compatible or not, may be introduced into the chamber 22 for adhesion of cells or tissues, or for studying interferences between this component and the already existing culture. This might be, for example, a gel, a collagen, a filter or any other support.

As indicated earlier, it is particularly advantageous when the lid 76 is transparent, so that direct observation with a microscope is possible during the whole culture period. For this purpose, the different constituents of the device, whether the tanks, the pressurization blocks or even the wells, are miniaturized so that they may be installed under a microscope objective lens.

Preferably, the lid 76 may be removed to have it replaced, or for removing cultivated cells or tissues in a sterile environment.

For preventing pressure changes within the culture chamber 22, upon removing the lid 76, a needle or any other device may be introduced in one or more openings 74 so as to establish communication between the inside of the culture chamber 22 and the surrounding external medium.

After removing the lid 76, the culture may be treated manually or automatically, according to different methods known to one skilled in the art.

Furthermore, the opening 74 may be used for establishing multiple, direct, automatic or manual communications within the culture chamber 22 for any fluid operation other than the one provided by the connecting means 20, 23 and 24 which supply the chambers with culture fluid. As an example, initial inoculation of the cells may be directly made through one or more openings 74.

Different treatments may thus be applied within the culture chambers of a same series. These openings 74 may also be used for connecting a chamber to several other chambers of a same series or of another series (when several devices in a facility are mounted in parallel).

Preferably, the tubes (or ducts) forming the connecting means, are made of a flexible elastomeric material so as to block culture fluid flow through squeezing, for example with a clamp.

In an alternative embodiment, certain of the wells may be configured so as to define two superimposed culture chambers separated by a flitter.

Reference is now made to FIGS. 10 and 11 in order to describe a first operating mode of the device and facility according to the invention. This first mode may be designated as a laminar mode. It consists of causing the culture fluid to flow upwards in the upper pocket of one of both tanks in order to establish a difference in height between this upper pocket and the lower pockets of both tanks, and then letting the culture fluid flow under gravity from the upper tank to the lower tanks, and in causing the culture fluid to flow upwards towards the upper pockets of the other tank. The same operations are again performed in the other direction ("backward direction"), so as to complete a cycle (or "reciprocation") between the two tanks, via the well. The number of cycles is selected according to the type of culture grown within wells 18.

The micro-controllers 50, 150 of the pressurization means are programmed, or configured for applying on each upper and lower pocket which they control, pressures defined by pressure sequences.

Preferably, these pressure sequences are stored beforehand in a rewritable memory of the micro-controller. In this case, programming (or in other words, storing the different sequences) is advantageously achieved via the RS232 interface which is connected to a microcomputer or the like. However, the micro-controller may be equipped with a non-rewritable memory, and in this case, it cannot be re-programmed with new sequences.

The laminar flow mode may be broken down into four step cycles illustrated in FIGS. 10A to 10H. Each step corresponds, for each pocket of each tank, to a period of the associated sequence.

In the first step illustrated in FIGS. 10H and 10A, the culture fluid which has just been injected into the first tank 2 is forced to reach the upper pocket 6. For this to occur, low pressure is applied on upper pocket 6 of the first tank 2, high pressures on lower pockets 7 and 29, while low pressure is applied on the upper pocket 27 of the second tank 25. The culture fluid is therefore forced to leave the upper pocket 27 of the second tank 25 in order to reach the upper pocket of first tank 2, via lower pockets 29 and 7. In other words, the upper pocket 27 of the second tank 25 is deflated whereas the upper pocket 6 of the first tank 2 is inflated, while filling up with culture fluid.

In the second step illustrated in FIGS. 10B and 10C, the culture fluid which has just been gathered in the upper pocket 6 of first tank 2 flows under gravity from the upper pocket 6 to the lower pocket 7 of the first tank then to the lower pocket 29 of the second tank 25. For this to occur, low pressure is applied on the upper pocket 6 of first tank 2 and high pressure is applied on the lower pocket 7 of this same tank, while low pressures are applied on the lower 29 and upper 27 pockets of the second tank 25. The upper pocket 6 is therefore deflated, whereas the lower pocket 29 of the second tank 25 is inflated while filling up with culture fluid.

In the third step illustrated in FIGS. 10D and 10E, the culture fluid which has just been gathered in the lower pocket 29 of the second tank 25 is forced to reach the upper pocket 27. For this to occur, low pressure is applied on the upper pocket 6 of first tank 2, high pressures on lower pockets 7 and 29, and low pressure on the upper pocket 27 of the second tank 25. The lower pocket 29 is therefore deflated, whereas the upper pocket 27 of the second tank 25 is inflated while filling up with culture fluid.

In the fourth step illustrated in FIGS. 10F and 10G, the culture fluid which has just been gathered in the upper pocket 27 of the second tank flows under gravity from the upper pocket 27 to the lower pocket 7 of the first tank 2. For this to occur, low pressures are applied on upper pockets 6 and 27 and on the lower pocket 7 of the first tank, while high pressure is applied on the lower pocket 29 of the second tank 25. The upper pocket 27 is therefore deflated, whereas the lower pocket 7 of the first tank 2 is inflated while filling up with culture fluid. This completes the "reciprocation" cycle.

The beginning of the first step is illustrated in FIG. 10H.

The four steps of the laminar mode are grouped together as a "reciprocation" cycle in FIG. 11. The number of successive cycles is selected according to the type of culture grown.

Reference is now made to FIGS. 12A to 12D in order to describe a second operating mode of a device or facility according to the invention.

In this so-called "turbulent" operating mode, high pressure is permanently applied on lower pockets 7 and 29 of the first 2 and second 25 tanks. In other words, the first and second upper sequences of the upper pockets of the first and second tanks comprise a succession of four periods of low pressure. This mode only consists of two steps.

In the first step illustrated in FIGS. 12A and 12D, low pressure is applied on the upper pocket 6 of the first tank 2 and high pressure is applied on the upper pocket 27 of the second tank 25. The fluid is therefore forced to reach the upper pocket 7 of the first tank 2, so that upper pocket 27 is deflated whereas upper pocket 6 is inflated.

In the second step illustrated in FIGS. 12B and 12C, high pressure is applied on the upper pocket 6 of the first tank 2 and low pressure on the upper pocket 27 of the second tank 25. The fluid is therefore forced to reach the upper pocket 27 of the second tank 25, so that upper pocket 6 is deflated whereas upper pocket 27 is inflated.

The beginning of the first step is illustrated in FIG. 12D.

Both steps of the turbulent mode are grouped together as a "reciprocation" cycle in FIG. 13. The number of successive cycles is selected according to the type of culture grown.

In FIG. 14, an alternative "reciprocation" cycle (between the two tanks) of the second turbulent operating mode is illustrated. In this alternative embodiment, high pressure is no longer permanently maintained on both lower pockets 7 and 29, but on both upper pockets 6 and 27. Very fast culture fluid flow is thereby obtained between both lower pockets 7 and 29, as said fluid cannot flow upwards, owing to the high pressures in upper pockets 6 and 27.

In this alternative embodiment, two steps are still provided.

In the first step (a and d), high pressure is applied on both upper pockets 6 and 27 and on the lower pocket 29 of the second tank, whereas low pressure is applied on the lower pocket 7 of the first tank 2.

In the second step (b and c), high pressure is applied on both upper pockets 6 and 27 as well as on the lower pocket 7 of the first tank 2, whereas low pressure is applied on the lower pocket 29 of the second tank 25. At the end of this step, the first step (c and a) may be started afresh.

The number of successive cycles is also selected according to the type of culture grown.

In another alternative turbulent operative mode (not shown), the first sequence applied to each pocket of the first tank consists of an alternation of first high pressure periods and second low pressure periods and the second sequence applied to each pocket of the second tank consists of an alternation of first low pressure periods and second high pressure periods.

Both laminar and turbulent operating modes, which have just been described, as well as the alternative mode, are only a few of the great number of examples which may be considered. It would thus be possible to combine turbulent operating cycles with laminar operating cycles.

Each of these different operating modes forms a step of the method according to the invention, including a preliminary step which consists of using one of the devices described above. In other words, the invention also relates to a method consisting of a first step wherein one of the devices according to the invention is provided and of a second step wherein one of the laminar or turbulent operating modes or a combination of the latter is applied to this device.

In this second step, substantially identical durations may be selected for the first periods of the first and second sequences and substantially identical durations may be selected for the second periods of the first and second sequences.

Furthermore, in the second step, the first upper sequence applied to the upper pocket of the first tank may consist of a sequence repeated a selected number of times, of the first, second, third and fourth periods of low pressure, whereas, firstly, the first lower sequence applied to the lower pocket of the first tank consists of a sequence repeated said selected number of times of a first high pressure period, of a second high pressure period, of a third high pressure period and of a fourth low pressure period, secondly, the second lower sequence applied to the lower pocket of the second tank consists of a sequence repeated said selected number of times of a first high pressure period, of a second low pressure period, of a third high pressure period and of a fourth high pressure period, and thirdly, the second upper sequence applied to the upper pocket of the second tank consists of a sequence repeated said selected number of times of first, second, third and fourth low pressure periods. Preferably, in this case, during the second step, durations of the first periods of the first and second, upper and lower sequences are substantially identical, durations of the second periods of the first and second, upper and lower sequences are substantially identical, durations of the third periods of the first and second, upper and lower sequences are substantially identical and durations of the fourth periods of the first and second, upper and lower sequences are substantially identical.

The invention applies to a great number of types of cells and tissues, such as notably:
intestinal cells: Intestine 407, Caco-2, Colo 205, T84, SW1116, WiDr, HT29, HT 115, HT 55;
endothelial cells: HAOSMC (Human Aortic Smooth Muscle Cells);
epidermal cells: NHEK-Neopooled (Human Epidermal Keratinocyte Neonatal), Equine Dermis;
cancer cells: HeLa, CHO-K1;
fibroplastic cells of the intestinal type: CCD-18Co;
fibroplastic cells of type MRC-5, 3T3, Wi-38;
myeloma: SP2O-Ag14, P3X63 Ag8 653, MPC11;
hybridoma;
insect cells: SF9.

This list is absolutely not exhaustive; these are only examples.

The invention is not limited to the embodiments of the device, the facility and the method described above, only given as examples, but it encompasses all alternative embodiments which may be considered by one skilled in the art within the scope of the claims hereafter.

What is claimed is:

1. A cell and tissue culture device comprising at least a culture well (18-i) defining a chamber (22-i) able to receive cells or tissues to be grown, having first (2) and second (25) tanks, wherein at least one of these tanks is configured to receive a culture fluid, and connecting structure (20,23,24) coupled to said well and said first and second tanks so as to enable the culture fluid to flow from one tank to another via said well,
   wherein each tank (20,25) accommodates at least one flexible pocket (6,7;27,29), wherein at least one of the pockets of these tanks is able to receive the culture fluid and said device comprises at least a controller module (50,150) able to provide first or second sequences of external pressures to be applied on the pockets of first and second tanks, respectively, and pressurization equipment (38,40–49,50–56,61–63) configured for applying to said pockets the pressures defined by said first and second sequences provided by the controller module, so as to control culture fluid flow in said well.

2. A device according to claim 1, characterized in that said first (2) and second (25) tanks each comprise an upper portion (3,26) and a lower portion (4, 28) connected with one another by a narrow intermediate portion (5,30), wherein each upper and lower portion of first and second tanks accommodate a flexible pocket, said upper (6,27) and lower (7,29) flexible pockets communicate with one another via the intermediate portion (5,30), and said connecting structure (20,24) communicates with lower pocket (6,29).

3. A device according to claim 2, characterized in that said controller module (50,150) is able to provide a first sequence of upper external pressures for the upper pocket (6) of the first tank (2), a first sequence of lower external pressures for the lower pocket (7) of the first tank (2), a second sequence of external lower pressures for said lower pocket (29) of the second tank (25) and a second sequence of upper external pressures for the upper pocket (27) of the second tank (25), and in that said pressurization equipment (38,40–49,51–56, 61–63) is configured for applying to said upper (6) and lower (7) pockets of the first tank (2), pressures from said first sequences of upper and lower pressures respectively and to said lower (29) and upper (27) pockets of the second tank (25), pressures from said second sequences of lower and upper pressures, respectively, in order to control the culture fluid flow in said well.

4. A device according to claim 2, characterized in that said upper levels of said upper flexible pockets (6,27) are substantially identical in design and said lower levels of said lower flexible pockets (7,29) are substantially identical in design.

5. A device according to claim 1, characterized in that said pockets (6,7,27,29) are permeable to gases, at least in the direction pointing from the outside to the inside.

6. A device according to claim 2, characterized in that said upper (6) and lower (7) pockets of the first tank (2), second tank (25), respectively, communicate through a duct (8,31) accommodated in the intermediate portion (5,30).

7. A device according to claim 6, characterized in that at least one of the first (2) and second (25) tanks includes an adapted opening (15) able to allow said culture fluid to be fed into the communication duct (8,31) between the pockets.

8. A device according to claim 2, characterized in that at least one of the upper portions (6,29) of the tanks includes an upper port (10) configured for connecting the upper pocket (6,29) which it accommodates, to a culture fluid feed and/or extraction device.

9. A device according to claim 8, characterized in that it comprises first access control structure (11,33), driven by the controller module (50,150) and able to control access to said upper pocket (6,27) via said upper port (10).

10. A device according to claim 2, characterized in that each lower tank portion (4,28) includes a lower port (17) able to connect said connecting structure (20,24) to the lower pocket (7,29) which it accommodates, and in that it comprises second access control structure (13,35), driven by the controller module (50,150) and able to control access to said lower pockets via said lower port (17).

11. A device according to claim 2, characterized in that upper (3,26) and lower (4,28) portions of first (2) and second (25) tanks each include a leak-proof inlet (59), and in that said pressurization equipment comprises a first pressurization circuit (40–43,46,47,56,58) able to supply with high pressure fluid, under the control of upper (47,147) and lower (46,146) valves driven by the controller module (50), each upper (3,26) and lower (4,28) portion of first and second tanks, via said leak-proof inlets (59,17).

12. A device according to claim 2, characterized in that upper (3,26) and lower (4,28) portions of first (2) and second (25) tanks each include a leak-proof inlet (59) and in that said pressurization equipment comprises a first pressurization circuit (40) including a fluid pump (41) and able to supply with high pressure fluid, under the control of upper (47) and lower (56) valves driven by the controller module (50), each upper and lower portion of the first tank, via said leak-proof inlets, as well as a second pressurization circuit (140) including a fluid pump (141) and able to supply with high pressure fluid, under the control of upper (147) and lower (156) valves driven by the controller module (150), each upper and lower portion of the second tank, via said leak-proof inlets.

13. A device according to claim 11, characterized in that said first (11,33) and second (13,35) access control structures comprise a duct (64) provided with a thinned flexible area (66) accommodated within a recess (60) and in that each pressurization circuit comprises two other valves (48, 49;148,149) able to supply with high pressure fluid the housings (60) of first and second access control structures on command from said controller means, in order to act on said thinned area (66) so as to vary the state of the associated access control structure.

14. A device according to claim 11, characterized in that said pressurization equipment comprises another pressurization circuit connected to said upper and lower valves, and able to supply with low pressure fluid, under the control of the controller module, each upper and lower portion of the first and second tanks.

15. A device according to claim 12, characterized in that said pressurization equipment comprises a third pressurization circuit (51–55) connected to said upper (47) and lower (46) valves, and able to supply with low pressure fluid, under the control of the controller module (50), each upper and lower portion of the first tank (2), as well as a fourth pressurization circuit connected to said upper (147) and lower (146) valves and able to supply with low pressure fluid, under the control of the controller module, each upper and lower portion of the second tank (25).

16. A device according to claim 15, characterized in that each third and fourth pressurization circuit is connected to said other valves (61,62;161,162) so as to cooperate with said first (11;33) and second (13:35) access control structures.

17. A device according to claim 2, characterized in that it comprises at least two wells (18-i) placed in series and communicating with each other by said connecting structure (23), wherein one of the wells (18-1) is connected to said first tank (2) and the other well (18-3) is connected to said second tank (25).

18. A device according to claim 17, characterized in that it comprises a third well (18-3) placed in series between both other wells and communicating with them through said connecting structure (23).

19. A device according to claim 2, characterized in that said connecting structure (20,23,24) comprises ducts, an end of which at least opens into a selected well culture chamber (22-i).

20. A device according to claim 17, characterized in that said wells (18-i) are independent units assembled together.

21. A device according to claim 17, characterized in that said wells (18-i) are configured on a plate (66).

22. A device according to claim 1, characterized in that each culture chamber (22-i) includes at least a transparent wall (76) configured so as to enable the cells or tissues to be observed during the culture process.

23. A device according to claim 1, characterized in that at least certain of the wells are configured so as to define two superimposed culture chambers separated by a filter.

24. A device according to claim 1, characterized in that the controller module (50:550) comprises a memory of the rewritable type able to store said pressure sequences.

25. A cell and tissue culture facility, characterized in that it comprises at least two devices (1-i) according to claim 1, placed in parallel, and a control unit able to drive together the control units (50-i,150-i) of said devices.

26. A facility according to claim 25, characterized in that certain wells of a device communicate with at least another well of another device, via said connecting structure.

27. A method for cell and tissue culture, comprising a first step wherein a culture device is provided, including at least one culture well able to receive cells or tissues to be grown, having first and second tanks coupled to the well, wherein at least one of these tanks is configured for receiving a culture fluid, characterized in that in the first step, at least a flexible pocket is accommodated in each tank, with at least one of these pockets able to receive the culture fluid, and in that it includes a second step wherein pressures defined by first and second sequences of selected pressures are applied to said pockets, in order to control the culture fluid flow in said well.

28. A method according to claim 27, characterized in that in the first step, an upper portion and a lower portion connected with one another by a narrow intermediate portion and each accommodating a flexible pocket, are provided in each tank, wherein said upper and lower pockets communicating with one another via the intermediate portion and said lower pockets are coupled to the well, and in that in the second step, pressures defined by first sequences of selected upper and lower pressures are applied on said upper and lower pockets of the first tank, respectively, and pressures defined by second sequences of lower and higher selected pressures are applied on said lower and upper pockets of the second tank, so as to control the culture fluid flow in said well.

29. Method according to claim 27, characterized in that in the second step, the first sequence applied to each pocket of the first tank, consists of an alternation of first high pressure periods and of second low pressure periods and the sequence applied to each pocket of the second tank consists of an alternation of first low pressure periods and second high pressure periods.

30. Method according to claim 28, characterized in that in the second step, the first sequence applied to the upper pocket of the first tank consists of an alternation of first low pressure periods and of second high pressure periods, and the second sequence applied to the upper pocket of the second tank consists of an alternation of first high pressure periods and second low pressure periods, and in that first and second sequences applied to lower pockets of the first and second tanks respectively, consists of a succession of high pressure periods.

31. Method according to claim 28, characterized in that in the second step, the first sequence applied to the lower pocket of the first tank, consists of an alternation of first low pressure periods and of second high pressure periods, and the second sequence applied to the lower pocket of the second tank consists of an alternation of first high pressure periods and of second low pressure periods and in that the first and second sequences applied to upper pockets of the first and second tanks respectively, consists of a succession of high pressure periods.

32. A method according to claim 29, characterized in that in the second step, the durations of the first periods of first and second sequences are substantially identical and the durations of the second periods of the first and second sequences are substantially identical.

33. A method according to claim 28, characterized in that in the second step:

the first upper sequence applied to the upper pocket of the first tank consists of a sequence repeated for a selected number of times of the first, second, third and fourth periods of low pressure;

the first lower sequence applied to the lower pocket of the first tank consists of a sequence repeated said selected number of times of a first high pressure period, of a second high pressure period, of a third high pressure period and of a fourth low pressure period;

the second lower sequence applied to the lower pocket of the second tank consists of a sequence repeated said selected number of times of a first high pressure period, of a second low pressure period, of a third high pressure period and of a fourth high pressure period; and the second upper sequence applied to the upper pocket of the second tank consists of a sequence repeated said selected number of times of a first, second, third and fourth low pressure periods.

34. A method according to claim 33, characterized in that in the second step, the durations of the first periods of the first and second, upper and lower sequences are substantially identical, the durations of the second periods of the first and second, upper and lower sequences are substantially identical, the durations of the first periods of the first and second, upper and lower sequences are substantially identical and the durations of the fourth periods of the first and second, upper and lower sequences are substantially identical.

* * * * *